United States Patent [19]

Ohlson

[11] Patent Number: 4,759,048
[45] Date of Patent: Jul. 19, 1988

[54] ARRANGEMENT IN COUNTER-WEIGHT BALANCED X-RAY FRAME STRUCTURES

[75] Inventor: Carl E. Ohlson, Solna, Sweden

[73] Assignee: AO Medical Products AB, Stockholm, Sweden

[21] Appl. No.: 16,385

[22] PCT Filed: May 28, 1986

[86] PCT No.: PCT/SE86/00246
§ 371 Date: Jan. 29, 1987
§ 102(e) Date: Jan. 29, 1987

[87] PCT Pub. No.: WO86/06950
PCT Pub. Date: Dec. 4, 1986

[30] Foreign Application Priority Data

May 31, 1985 [SE] Sweden .................. 8502712

[51] Int. Cl.⁴ ............................. H05G 1/02
[52] U.S. Cl. .................. 378/197; 378/193; 378/196
[58] Field of Search ............ 378/197, 196, 193, 189

[56] References Cited

U.S. PATENT DOCUMENTS 3,770,955 11/1973 Tomita et al. .................. 378/197
4,127,775 11/1978 Ohlson .......................... 378/197

FOREIGN PATENT DOCUMENTS 0745010 2/1956 United Kingdom .............. 378/197

Primary Examiner—Janice A. Howell
Assistant Examiner—David P. Porta
Attorney, Agent, or Firm—Fleit, Jacobson, Cohn & Price

[57] ABSTRACT

A counter-weight balanced X-ray frame (1) has a vertical column (2) on which a pendulum arm (3) carrying X-ray equipment (4, 5) is mounted for vertical movement therealong and rotational movement therearound. A brake disc (10) for arresting rotational movement and actuated by a magnetic brake (11) is incorporated in a centering mechanism adapted to seek one or more pre-determined positions for the pendulum arm, e.g. when it forms an angle with the frame of 0°, 90°, 180° or 270°, without the operator needing to interfere in the sequence of movements. When the relevant setting position is approached, the operator need only carry out the operating movement which activates corresponding brake means—for example releases a corresponding operating handle on the pendulum arm—whereupon the pendulum arm itself adopts the pre-determined setting position.

7 Claims, 1 Drawing Sheet

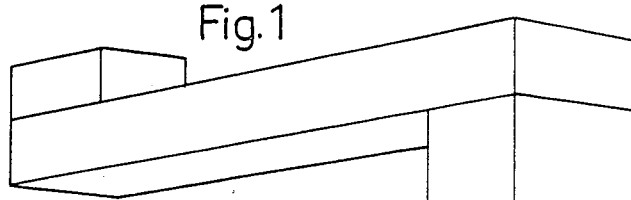
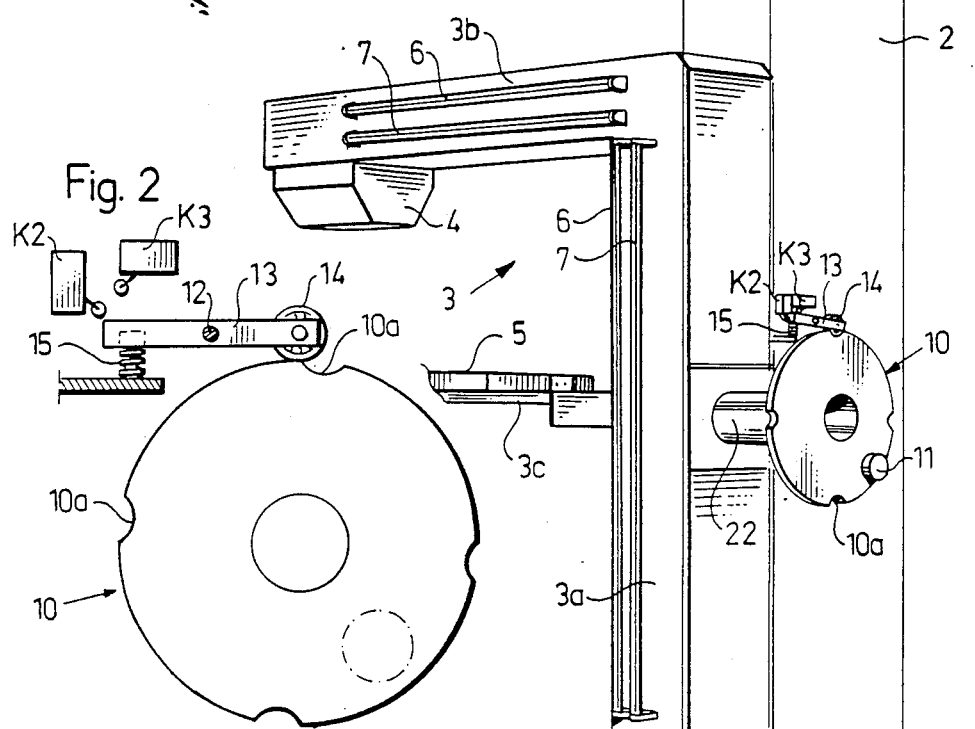
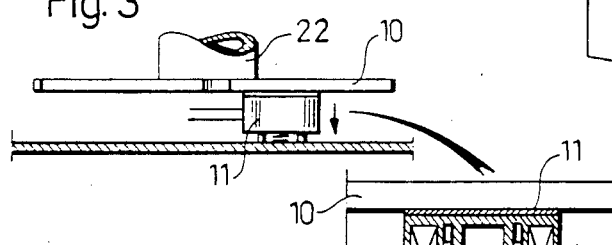
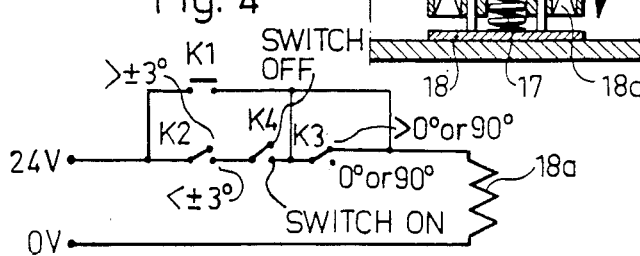

ARRANGEMENT IN COUNTER-WEIGHT BALANCED X-RAY FRAME STRUCTURES

The present invention relates to an arrangement in counter-weight balanced X-ray frame structures of the kind which include an upright column on which a pendulum arm carrying X-ray equipment is mounted for vertical movement therealong and journalled for rotational movement in relation thereto; at least one, preferably automatically applied brake means for arresting movement of the pendulum arm in the axial direction of the column and at least one, preferably automatically applied brake means for arresting rotational movement of the pendulum arm in a selected position of rotation relative to the frame structure.

An X-ray frame structure of the aforesaid kind provided with a pendulum arm can either be supported on the floor or suspended from the ceiling of a room, and may have varying forms, depending upon the requirements placed thereon from case to case.

As a rule, it is preferred to display the position to which the pendulum arm has been displaced along the column and rotated relative thereto in analogue or digital terms, so that the operator—who sets the arm manually to the position desired for a given type of X-ray photograph—is constantly informed of the position of the pendulum arm and is warned when the arm begins to approach the desired setting.

BACKGROUND PRIOR ART

A counter-weight balanced X-ray frame structure of the aforedescribed kind is described in SE-C-7414800-8 and patent of addition SE-C-7605920-3 (both AO:s Metall & Mek. Verkstad). In this known kind of X-ray frame structure two longitudinally extending handles stretch along the major part of the length of the arm, of which handles one incorporates components for generating an operating field for releasing rotational movement of the arm, while the other handle incorporates components for generating a field for releasing the movement of the arm axially along the column.

Thus, when holding the one handle the arm can be moved vertically to a desired position, while when holding the other handle the arm can be swung to a desired rotational position. Naturally, both of these movements can be carried out simultaneously. As soon as one of the handles is released, the corresponding brake means is activated, so that the arm stops in the position occupied by the arm when the handle is released.

In other types of known X-ray frame structures, the release and application of corresponding brake means is effected by actuating switches provided on the arm and/or the frame structure.

When using an X-ray frame of the aforesaid kind in practice it is found that a number of arm setting positions occur relatively often. Consequently, there is a need for the possibility of setting one or more such positions in a more convenient manner, so that the operator can be relieved from a large part of the work associated with fine adjustment to the setting of the pendulum arm, and so that the operator can be made aware of whether or not the arm has actually reached the position desired, without having to make exhaustive checks in this respect.

This problem applies with all types of X-ray frames provided with pendulum arms, i.e. both when the arms are arrested at the moment when the operator releases a handle and when the operator is forced to manipulate one or more switches in order to activate or de-activate the braking function.

OBJECT OF THE INVENTION

The object of the present invention is to provide a simple and reliable solution to the aforesaid problem, this solution being applicable irrespective of the manner in which the means for arresting rotational movement of the arm is activated.

SUMMARY OF THE INVENTION

An arrangement according to the invention which fulfils the aforesaid object and other objects is mainly characterized in that the brake means for arresting rotary movement of the arm is arranged to co-act with a centering mechanism which upon normal operational movement for applying the braking means somewhere within a range relating to one or more pre-determined positions, e.g. when the arm forms angles of 0°, 90°, 180° or 270° with the frame, causes the arm to seek and be stopped in the predetermined position.

Thus, when applying the invention the operator need not set the rotational position of the arm with any degree of accuracy. When the arm approaches the relevant setting position—which can be read-off by the operator, e.g. on a digital indicator on the frame—the operator need only carry out the normal operational movement for arresting arm movement, for example release his grip on the handle, which co-acts electrically/inductively with the brake means for said rotary movement, or activates corresponding switches, whereupon the centering mechanism "takes over" and ensures that the arm is caused to adopt precisely the pre-determined position, the arm being subsequently locked in this position.

Thus, the more frequently rotational positions of the arm can be set with greater accuracy, while simultaneously relieving the operator of this responsibility.

In accordance with one embodiment of the invention preferred in practice the centering mechanism includes a circular plate which can be rotated about the geometric rotational axis of the arm and which is provided around its periphery with approximately semi-cylindrical recesses corresponding to the pre-determined position or positions and adapted to receive at least partially a centering wheel rotatably carried by a pivotable arm, said wheel being held pressed against the periphery of the circular plate, for example by means of a spring acting on the pivotable arm.

The centering mechanism according to this embodiment is structurally simple and is highly reliable in practice, since the co-action between a wheel of the aforesaid kind—which in practice suitably comprises a ball bearing—and a peripheral recess in the circular plate adapted to the wheel enables the position of the pendulum arm to be accurately determined and also enables large forces to be transferred from the spring acting on the wheel via said pivotable arm.

The pendulum arm is often very large with a subsequent considerable mass, and consequently it will be understood that, in many instances, it must be possible to apply large forces in order to arrest the movement of the pendulum arm and to cause the pendulum arm to swing back precisely to the pre-determined position subsequent to the arm having passed said position.

A centering mechanism of the aforedescribed kind, however, also affords the advantage that the arm and-/or the wheel when executing a pivotal movement, when the wheel enters a peripheral recess, there is activated one or more electric circuits which are superimposed on the electrical circuit or circuits which activate the means for arresting rotary movement of the pendulum arm in response to the aforesaid normal operational braking movement.

Thus, in this respect an arrangement according to the invention constitutes a combination of mechanical and electromagnetic influence in causing the pendulum arm to stop and be locked in the desired setting position.

Accordingly, a preferred embodiment of the invention is characterized in that an electric circuit of the aforesaid kind is activated when the wheel begins to enter a recess and disengages the circuit which activates the braking means for rotational movement in response to normal operational braking movement, whereupon, when the wheel reaches the bottom of the recess, a further circuit is activated so as to momentarily apply the braking means, so as to retard the rotational movement of the pendulum arm.

In this case it is preferred that the pressure exerted against the wheel via the arm is of such magnitude that the wheel, subsequent to passing the bottom position without leaving the recess, presses back the circular plate and the pendulum arm in opposite directions, so as to further apply the braking means momentarily in the bottom position of the wheel etc., until the pendulum arm stops and is precisely locked in the pre-determined position.

Movement of the circular plate and the pendulum arm in connection with the engagement of the wheel in the recess may correspond to approximately 1°–5° approximately 3° of rotational movement of the pendulum arm on either side of the pre-determined rotational position.

An advantage is afforded in many cases when a brake disc for arresting rotary movement of the pendulum arm is incorporated in the centering mechanism. In other words the same disc is used both as a brake disc and as a centering mechanism. It is possible, however, to utilize two separate discs, which are then positioned concentrically and carried by the same shaft.

The brake means used is suitably a magnetic brake, which may be of any suitable kind and caused to engage the brake disc by means of a suitable friction element.

An embodiment of the invention will now be described with reference to the accompanying schematic drawings.

FIG. 1 is a partially cut-away perspective view of a counter-weight balanced X-ray frame provided with an arrangement according to the invention.

FIG. 2 is a schematic view illustrating the principle of the centering mechanism used in accordance with the invention.

FIG. 3 illustrates schematically an embodiment of a brake mechanism for the pendulum arm.

FIG. 4, finally, is a circuit diagram illustrating the principle of the co-action between a number of electrical circuits utilized when applying the invention.

DESCRIPTION OF A PREFERRED EMBODIMENT

FIG. 1 illustrates an X-ray frame which is suspended from a ceiling and which includes a vertical part or column 2, on which a pendulum arm 3 is mounted for vertical movement along said column and journalled for rotational movement relative thereto. The pendulum arm comprises a part 3a which is parallel with the column 2, and two opposing horizontal parts 3b, 3c which carry X-ray equipment 4,5.

The pendulum arm 3 is balanced by a counter-weight and is provided with an automatically applied brake (not shown) for preventing movement of the pendulum arm along the column, and an automatically applied brake 10,11 for preventing rotational movement of the pendulum arm relative to the column. In the illustrated embodiment, the brakes are released electromagnetically with the aid of an electric operating field, which when approached or touched by, for example, a hand or an object releases a corresponding brake, so that the pendulum arm 3 can be rotated and/or displaced in the axial direction of the column. Two elongated handles 6,7 extend along the pendulum arm, of which handles one (6) incorporates components for generating an operating field effective for releasing the pendulum arm for rotational movement, and the second handle (7) incorporates components for generating the field for releasing the pendulum arm for said axial movement.

The brake for arresting rotational movement of the pendulum arm comprises a circular plate 10 carried on a tubular shaft 12, which shaft also carries the pendulum arm 3, such that the tubular shaft 12 and the circular disc 10 have the same geometric axis.

When the handle 6 is released, an electromagnetic brake 11 engages the circular plate 10 so as to prevent or arrest movement of the pendulum arm.

The circular plate 10 also forms part of a centering mechanism, the purpose of which is to cause the pendulum arm to seek the relevant pre-determined position and to be locked in said position when the handle 6 is released somewherein the vicinity of one or more pre-determined positions, corresponding to the position of recesses 10a in the periphery of the circular plate 10.

In the illustrated embodiment, there are provided four such recesses 10a, these recesses corresponding to angular positions of 0°, 90°, 180° and 270° of the pendulum arm to the frame 2.

The principle according to which the centering mechanism operates can best be seen from FIG. 2.

In addition to the circular plate 10 and the peripheral recesses 10a the centering mechanism comprises an arm 13 which can be swung about a pivot axis 12 and which carries at one end a centering wheel in the form of a ball race 14, the radius of which corresponds to the radius of the semi-cylindrical recesses 10a in the circular plate 10.

A powerful thrust spring 15 is arranged to bias the arm 13 in a manner to urge the wheel 14 against the periphery of the circular plate 10.

When the operator swings the pendulum arm 3, the circular plate 10 is swung simultaneously relative to the arm 13 and the centering wheel 14, whereupon the wheel 14 runs around the periphery of the circular plate.

When the pendulum arm approaches a pre-determined setting position of the aforedescribed kind, the wheel 14 is pressed down into a corresponding recess 10a, and gradually ensures that the pendulum arm is stopped in precisely the desired position, without the operator needing to take further action.

This is achieved in the illustrated embodiment in that the end of the arm 13 opposite the wheel 14, in dependence on the pivotal position of the arm determined by the position of the wheel in relation to one of the recesses 10a, activates first the one and then the other of two switches K2 and K3 respectively, forming part of electrical circuits of the kind illustrated in FIG. 4.

Thus, as will be seen, the circuits incorporating the switches K2 and K3 are superposed on the electrical circuits which activate the brakes 10,11 in response to normal operational braking movements.

For example, the circuit incorporating the switch K2 is activated when the wheel 14 begins to enter a recess 10a. At this stage the circuit which activates the brakes 10,11 with normal operational braking movement is disconnected, whereupon when the wheel 14 reaches the bottom of the recess 10a a further circuit, namely the circuit incorporating the switch K3 is activated. Thus, the brakes 10,11 are temporarily applied so as to retard the rotational movement of the pendulum arm.

The pressure at which the wheel 14 is urged towards the recess 10a by the spring 15, via the arm 13, is of such magnitude that subsequent to the wheel 14 passing the bottom position in the recess the circular plate 10 is forced back together with the pendulum arm 3 in the opposite direction, without the wheel leaving the recess. As the wheel again passes the bottom position, the brakes are again momentarily applied, and an additional corresponding sequence of movement may possibly occur before the wheel 14 stops in its bottom position in the relevant recess 10a, the pendulum arm thus being arrested in precisely the pre-determined position.

Engagement of the wheel 14 in the recess 10a corresponds to a rotational movement of the pendulum arm through about 3° on each side of the centre of the recess. In other words, this means that the operator—who is able to read the prevailing rotational position of the pendulum arm on a digital scale—can release the operating handle 6 when the pendulum arm is located at about 3° from the desired pre-determined position. The aforedescribed centering mechanism then takes over the sequence of movements in the aforedescribed manner, i.e. the brakes 10,11 are de-activated with the exception of those instances when they are momentarily applied when the wheel 14 is located in the bottom of the recess 10a, whereafter the brakes are finally and definitely applied subsequent to the pendulum arm having reached precisely the position desired.

Thus, in operation, the pendulum arm automatically seeks the correct position without requiring the operator to take part.

FIG. 3 illustrates an embodiment of a simple magnetic brake arrangement capable of being used when applying the invention. The figure is intended solely to illustrate in principle the manner in which the brakes are applied by means of a thrust spring 17, wherewith subsequent to application of the brake the pulling magnet 18 ensures that the brake shoe 11 moves to its release position.

However, as beforementioned, other types of braking arrangements may be utilized with the invention.

FIG. 4 is a circuit diagram illustrating how the circuits incorporating the switches K2 and K3 co-act with one another to energize the coil 18a of the electromagnet 18. Thus, the switch K1 is included in the circuit which inductively applies the brake for arresting pivotal movement of the pendulum arm when the handle 6 is released.

The switches K2 and K3 are incorporated, in the aforedescribed manner, in circuits which are superposed on said circuits. Finally, the switch K4 is intended for switching-in and switching-out the self-centering regions, i.e. the regions of about 3° before and after the relevant "pre-determined position", and which in the illustrated embodiment is corresponded by entrance of the wheel 14 into the recess 10a.

INDUSTRIAL APPLICATION

As will be understood from the aforegoing, a centering arrangement according to the invention can be used with various types of X-ray stands or frames, irrespective of the manner in which the brakes provided for arresting rotational movement of the pendulum arm are activated or de-activated. In addition to the aforementioned advantages, the invention affords, inter alia, the further advantage that the thrust spring—referenced 16 in the illustrated embodiment—which carries out the mechanical centering work need not be robustly constructed. If such were the case, a considerable drawback would be presented when attempting to swing the frame back to another position subsequent to the aforesaid automatic centering in a pre-determined position. The momentary automatic application of the brake means in the centering position in accordance with the invention eliminates the need of a powerful spring of the aforesaid kind. Consequently, it is the aforesaid combination of a mechanical centering arrangement and an electromagnetically achieved momentary and automatic application of the brake arrangement which affords this particular advantage.

I claim:

1. An arrangement in counter-weight balanced X-ray frame structures comprising a column on which a pendulum arm carrying X-ray equipment is arranged for vertical movement therearound; at least one brake means for arresting movement of the pendulum arm along the column; and at least one brake for arresting rotational movement of the pendulum arm in selected rotational positions of the pendulum arm relative to the frame, characterized in that the brake for arresting rotational movement of the pendulum arm co-acts with a centering mechanism having means for arresting the pendulum arm in at least one predetermined angular position relative to the column, and centering means for causing the pendulum arm to seek said predetermined position from preset angular positions on opposite sides thereof.

2. An arrangement according to claim 1, characterized in that the centering means includes a circular plate which can be rotated around the geometric pivot axis of the pendulum arm and which has provided around its perpihery at least one semi-cylindrical recess corresponding to the predetermined position and adapted to receive at least partially a centering wheel rotatablay carried by a pivotable arm, said centering wheel being held pressed against the periphery of the cylindrical plate by means acting on the arm.

3. An arrangement according to claim 2, characterized in that one of the arm and the wheel during pivotal movement, when the wheel enters the recess, activates at least one electrical circuit which is superposed on circuit means which, upon normal operational braking movement, activate the brake for arresting rotational movement of the pendulum arm.

4. An arrangement in counter-weight balanced X-ray frame structures comprising a column on which a pendulum arm carrying X-ray equipment is arranged for vertical movement therealong and journalled for rotational movement therearound; at least one brake means for arresting movement of the pendulum arm along the column; and at least one brake for arresting rotational movement of the pendulum arm in selected rotational positions of the pendulum arm relative to the frame, characterized in that the brake for arresting rotational movement of the pendulum arm co-acts with a centering mechanism, having means for arresting the pendulum arm in at least one pre-determined angular position relative to the column, and centering means for causing the pendulum arm to seek said pre-determined position from preset angular positions on opposite sides thereof, an arrangement according to claim 1, characterized in that the centering means includes a circular plate which can be rotated around the geometric pivot axis of the pendulum arm and which has provided around its periphery at least one recess corresponding to the pre-determined position and adapted to receive at least partially a centering wheel rotatably carried by a pivotable arm, said centering wheel being held pressed against the periphery of the cylindrical plate by means acting on the arm, characterized in that one of the arm and the wheel during pivotal movement, when the wheel enters the recess, activates at least one electrical circuit which is superposed on circuit means which, upon normal operational braking movement, activate the brake for arresting rotational movement of the pendulum arm, and characterized in that one circuit is activated by a switch when the wheel begins to enter the recess and disengages another circuit which, upon normal operational braking movement, activates the brake for arresting rotational movement of the pendulum arm, whereupon, when the wheel reaches the bottom of the recess, a further circuit is activated to cause momentary application of the brake so as to retard rotational movement of the pendulum arm.

5. An arrangement according to claim 4, characterized in that the pressure with which the wheel is urged towards the recess via the arm is of such magnitude that the wheel, subsequent to passing said bottom position without leaving the recess presses back the circular disc and the pendulum arm in opposite direction, therewith to further momentarily apply the brake arrangement in the bottom position of the wheel until the pendulum arm is arrested in the pre-determined position.

6. An arrangement according to claim 3, characterized in that the engagement of the wheel in the recess corresponds to a rotational movement of the pendulum arm of about 1°–5°, preferably about 3° on each side of the pre-determined setting position.

7. An arrangement according to claim 1, characterized in that a brake disc for arresting rotational movement of the pendulum arm is incorporated in the centering mechanism.

* * * * *